United States Patent [19]
Kim et al.

[11] Patent Number: 5,846,723
[45] Date of Patent: Dec. 8, 1998

[54] METHODS FOR DETECTING THE RNA COMPONENT OF TELOMERASE

[75] Inventors: Nam Woo Kim, San Jose; Fred Wu, San Carlos; James T. Kealey, San Anselmo; Ronald Pruzan, Palo Alto; Scott L. Weinrich, Redwood City, all of Calif.

[73] Assignee: Geron Corporation, Menlo Park, Calif.

[21] Appl. No.: 770,565

[22] Filed: Dec. 20, 1996

[51] Int. Cl.[6] .............................. C12Q 1/68; C12P 19/34; C07H 21/04; C07H 21/02
[52] U.S. Cl. ........................... 435/6; 435/91.2; 435/91.3; 536/23.1; 536/24.3; 536/24.33
[58] Field of Search ............................. 435/6, 91.2, 91.3; 536/23.1, 24.3–24.33

[56] References Cited

U.S. PATENT DOCUMENTS 5,583,016  12/1996  Villeponteau et al. ................. 435/91.3

FOREIGN PATENT DOCUMENTS

WO 95/13381  5/1995  WIPO .
WO 96/01835  1/1996  WIPO ............................. C07H 21/00

OTHER PUBLICATIONS

Albanell, Juan, et al. (1996) "Telomerase Activity Is Repressed During Differentiation of Maturation–sensitive but not Resistant Human Tumor Cell Lines", *Cancer Research* 56:1503–1508.

Avilion, Ariel A., et al. (1996) "Human Telomerase RNA and Telomerase Activity in Immortal Cell Lines and Tumor Tissues", *Cancer Research* 56:645–650.

Villeponteau, Bryant (1996) "The RNA components of human and mouse telomerases", *seminars in Cell & Development Biology*, 7:15–21.

Harley, Calvin B., et al. (1995) "Telomeres and telomerase in aging and cancer", *Current Opinion in Genetics and Development*, 5:249–255.

Feng, Junli, et al. (1995) "The RNA Component of Human Telomerase", *Science*, 269:1236–1241.

Kim, Nam W., et al. (1994) "Specific Association of Human Telomerase Activity with Immortal Cells and Cancer", *Science*, 266:2011–2015.

Blasco, Maria A., et al. (1995) "Functional Characterization and Developmental Regulation of Mouse Telomerase RNA", *Science*, 269:1267–1270.

Bodnar, Andrea G., et al., (1996) "Mechanism of Telomerase Induction during T Cell Activation", *Experimental Cell Research*, 228:58–68 Article No. 0299.

Khan, Islam et al., (1992), "Polymerase chain reaction assay or mRNA using 28S IRNA as internal standard", *Neurosciences Letters*, 147:114–117.

*Primary Examiner*—W. Gary Jones
*Assistant Examiner*—Dianne Rees
*Attorney, Agent, or Firm*—Kevin R. Kaster; John R. Storella; Annette S. Parent

[57] ABSTRACT

Methods of detecting the RNA component of telomerase, diagnosing cancer, and determining its prognosis using polynucleotides that hybridize to the RNA component of mammalian telomerase in a sample.

38 Claims, 1 Drawing Sheet

```
GGGTTGCGGA GGGTGGGCCT GGGAGGGGTG GTGGCCATTT TTTGTCTAAC  50

CCTAACTGAG AAGGGCGTAG GCGCCGTGCT TTTGCTCCCC GCGCGCTGTT 100

TTTCTCGCTG ACTTTCAGCG GCGGAAAAG  CCTCGGCCTG CCGCCTTCCA 150
                                        ←―――――――――――― 21
                                              ←――――――― 20
CCGTTCATTC TAGAGCAAAC AAAAAATGTC AGCTGCTGGC CCGTTCGCCC 200
―――――――――21
―――――――――21ab
    ←――――ab 3
    ←――――ab 2
        ←ab1
    ←―――――――――――――20/21
    ←―――――――――RP3
                ←――――――――――――――――――RP2
CTCCCGGGGA CCTGCGGCGG GTCGCCTGCC CAGCCCCCGA ACCCGCCTG  250

GAGGCCGCGG TCGGCCCGGG GCTTCTCCGG AGGCACCCAC TGCCACCGCG 300
                                        ←―――――――――― 16
AAGAGTTGGG CTCTGTCAGC CGCGGGTCTC TCGGGGCGA GGGCGAGGTT 350
―――――――――――――――16
―――――――――――――――16ab
    ←――――――16bc
CAGGCCTTTC AGGCCGCAGG AAGAGGAACG GAGCGAGTCC CCGCGCGCGG 400
       ^
⌐_⌐―G――――――――――――――― 14                             14
        ←――――――― 14ab
⌐_⌐―G――――――――― 14bc
        ←――――14d
CGCGATTCCC TGAGCTGTGG GACGTGCACC CAGGACTCGG CTCACACATG 450
C                                                     451
```

*FIG. 1.*

METHODS FOR DETECTING THE RNA COMPONENT OF TELOMERASE

FIELD OF THE INVENTION

The present invention provides methods for detecting the RNA component of telomerase in cell samples, useful, e.g., for diagnosing cancer and determining its prognosis in mammals.

BACKGROUND OF THE INVENTION

Nearly all bodily cells possess finite capacity to divide and replicate. One mechanism that regulates this finite life span involves telomeres, which are specialized structures found at the end of chromosomes and which are composed of protein and DNA having the repeated sequence, TTAGGG. Telomeres shorten each time that a cell divides, until they become critically short. This event is associated with the onset of cell senescence, after which the cell ceases to proliferate. In contrast, certain cells are "immortal" and have the capacity to divide indefinitely. Such cells include, for example, single-celled eukaryotic organisms, germline cells (i.e., oocytes and sperm), certain human cell cultures, and cancer cells. These cells do not exhibit telomere shortening upon cell division. Most of these cells, including about 90% of primary cancers, exhibit the activity of an enzyme, telomerase. Mortal bodily cells exhibit very little or no telomerase activity. Telomerase is a ribonucleoprotein that regulates the length of telomeres. Telomerase acts as a DNA polymerase, adding telomeric repeat sequences to the chromosomes' ends using a sequence within the RNA component of telomerase as a template. The RNA component of human telomerase, hTR, has been isolated. Feng et al. (1995) *Science* 269:1236–41 and U.S. Pat. No. 5,583,016.

Due to the toll that cancer takes on human lives and the importance of early diagnosis, there is a continued need for new methods of determining the diagnosis and prognosis of cancer, such as methods involving telomerase detection. Monitoring changes in RNA expression, for example, the RNA component of telomerase, requires reliable methods of identifying and quantitating the target molecule. Such changes in expression can be examined by specific amplification of small amounts of RNA. However, variation in the amplification reaction may be magnified during subsequent amplification cycles, thus pointing to a need for internal controls. For example, 28S rRNA, which is separately reverse transcribed and then added to an amplification reaction, has been used as a co-amplification control (Khan et al., *Neuroscience Letters*, 147: 114–117 (1992)). Due to the toll that cancer takes on human lives and the importance of early diagnosis, there is a continued need for new methods of determining the diagnosis and prognosis of cancer.

SUMMARY OF THE INVENTION

Detection of the RNA component of telomerase is useful in determining whether a cell is cancerous. The present invention thus describes methods of detecting the presence, absence, or amount of the RNA component of telomerase in a sample. The present invention also provides methods for diagnosis and prognosis of cancer. Polynucleotides that specifically hybridize to accessible regions of hTR in the telomerase ribonucleoprotein can be used to detect the presence or absence, and the amount of hTR in a sample. In particular, a method of quantitation of a test polynucleotide such as hTR, using co-amplification of a test polynucleotide and a control polynucleotide, is useful for diagnosis and prognosis of cancer.

In one aspect, this invention provides a method for detecting hTR in a sample, which is carried out in two steps: (1) first, a sample is contacted with a polynucleotide comprising a sequence of at least 7 nucleotides that specifically hybridizes to hTR within a region of hTR that is accessible in the telomerase ribonucleoprotein but that does not specifically hybridize to a template region of hTR; and (2) the specific hybridization is detected. Specific hybridization provides a detection of hTR in the sample.

In one embodiment, accessible regions of hTR comprise nucleotide positions 137–196, 290–319, and 350–380 of hTR (see FIG. 1 and SEQ ID NO:1); the nucleotide sequence of the polynucleotide is also complementary to these accessible regions. In yet another embodiment, the polynucleotide has a sequence corresponding to SEQ ID NOS:2–14.

In another embodiment, the polynucleotide is a nucleotide analog selected from phosphorothioates, phosphoramidates, methyl phosphonates, chiral-methyl phosphonates, 2O-methyl ribonucleotides and peptide-nucleic acids.

In another embodiment, the sample can be a histological section of tissue and a sample that has been prepared for in situ detection.

In one embodiment, the polynucleotide includes a detectable moiety for determination of specific hybridization of the polynucleotide to hTR. The detectable moiety can be attached to the polynucleotide via a linker. The detectable moiety can be a fluorescent label, a radioactive label, an enzymatic label, a biotinyl group, or an epitope recognized by a secondary reporter.

In another embodiment, the polynucleotide is a primer that is used to initiation reverse transcription of hTR. Detection of hTR can be achieved by detection of an hTR reverse transcript, for example, by chain elongation of a sequence that is complementary to hTR with a nucleotide that includes a detectable moiety. The reverse transcript can also be detected by hybridization with a polynucleotide that is used as a probe and hybridizes to the reverse transcript. Detection of the reverse transcript can also be achieved by amplification of a sequence of hTR from the reverse transcript, for example, with a nucleotide that includes a detectable moiety. Detection of amplified hTR can also be achieved using a polynucleotide as a probe.

In another aspect, this invention provides a method of diagnosing cancer in a patient, which is composed of two steps: (1) determining a diagnostic value by detection of hTR in a patient sample, where detection of hTR uses the method of detection described herein; and (2) comparing the diagnostic value with a normal range of hTR in control cells, where a diagnostic value that is above normal range is diagnostic of cancer.

In one embodiment, the cancer is bladder, colon, breast, or prostate cancer.

In another aspect, this invention provides a method of providing a prognosis for a cancer patient, which includes two steps: (1) determining the amount of hTR per cancer cell in a patient sample using the method of detecting hTR described herein and correlating the amount with an amount per cancer cell in the sample; and (2) comparing the amount of hTR per cancer cell with a prognostic value of hTR per cancer cell consistent with a particular prognosis for the cancer, where an amount of hTR per cell in a sample that is at the prognostic value provides the particular prognosis.

In one embodiment, the cancer is neuroblastoma, colon, breast, or prostate.

In another aspect, this invention provides a method of determining the amount of hTR in a sample, which includes five steps: (1) amplifying hTR; (2) amplifying a control polynucleotide; (3) determining an amount of amplified control and amplified hTR in the sample; (4) normalizing the amount of amplified hTR with respect to the amount of the amplified control polynucleotide to produce a normalized amount of hTR; and (5) comparing the normalized amount of hTR to a standard, thus providing a determination of the amount of hTR in a sample.

In one embodiment, the control polynucleotide is rRNA, preferably 28S rRNA.

In another embodiment, the efficiency of amplification of the control polynucleotide is different than the efficiency of amplification of the test polynucleotide in the sample, and in yet another embodiment the efficiency of amplification of the control polynucleotide is less than the efficiency of amplification of the test polynucleotide in the sample.

In another embodiment, before amplification, both the test and the control polynucleotides are reverse transcribed under conditions where reverse transcription of the control polynucleotide is less efficient than the test polynucleotide.

In another embodiment, the combined efficiency of chain elongation of the control polynucleotide and its complement is less than the combined efficiency of chain elongation of the test polynucleotide and its complement. In yet another embodiment, the combined efficiency of initiating chain elongation of the test and the control polynucleotides and their complements is similar to the difference in the amount of test and control polynucleotide in the sample.

In another embodiment, the combined efficiency of hybridization of the primer to the control polynucleotide and its complement is less than the combined efficiency of hybridization of the primer to the test polynucleotide and its complement.

In another embodiment, reduced efficiency of reverse transcription, amplification, hybridization, and chain elongation is achieved by including mismatches at the 5' end of the primer, and by providing a relatively shorter primer for the control polynucleotide.

In one embodiment, the step of amplifying a sequence of hTR comprises amplifying a sequence of hTR from an accessible region of hTR, wherein the region comprises nucleotide positions 137–196, 290–319, and 350–380 of hTR (see FIG. 1 and SEQ ID NO:1). In yet another embodiment, the primers are selected from SEQ ID NOS:15–26.

BRIEF DESCRIPTION OF THE DRAWING

FIG. 1 presents the nucleotide sequence of the RNA component of human telomerase (nucleotides 266–715 of SEQ ID NO:1). The boxed areas, from nucleotides 137–196, 290–319 and 350–380, indicate regions of hTR accessible in the telomerase holoenzyme. Antisense molecules, indicated by numbers below the hTR sequence, have sequences complementary to the hTR sequence indicated by the arrows.

DETAILED DESCRIPTION

I. DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2d ed. 1994); *The Cambridge Dictionary of Science and Technology* (Walker ed., 1988); and Hale & Marham, *The Harper Collins Dictionary of Biology* (1991). Although any methods and materials similar or equivalent to those described herein can be used in the practice or testing of the present invention, preferred methods and materials are described. As used herein, the following terms have the meanings ascribed to them unless specified otherwise.

"Polynucleotide" refers to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an MRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of polypeptide sequences is the amino-terminus; the right-hand end of polypeptide sequences is the carboxyl-terminus.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

A "reference sequence" is a defined sequence used as a basis for a sequence comparison and may be a subset of a larger sequence, e.g., a complete cDNA, protein, or gene sequence.

Because two polynucleotides or polypeptides each may comprise (1) a sequence (i.e., only a portion of the complete polynucleotide or polypeptide sequence) that is similar between the two polynucleotides, or (2) a sequence that is divergent between the two polynucleotides, sequence comparisons between two (or more) polynucleotides or polypeptides are typically performed by comparing sequences of the two polynucleotides over a "comparison window" to identify and compare local regions of sequence similarity.

A "comparison window" refers to a conceptual segment of typically at least 12 consecutive nucleotide or 4 consecutive amino acid residues that is compared to a reference sequence. The comparison window frequently is at least 15 or at least 25 nucleotides in length or at least 5 or at least 8 amino acids in length. The comparison window may comprise additions or deletions (i.e., gaps) of about 20 percent or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Dr., Madison, Wis.) or by inspection, and the best alignment (i.e., resulting in the highest percentage of homology over the comparison window) generated by any of the various methods is selected.

A subject nucleotide sequence or amino acid sequence is "identical" to a reference sequence if the two sequences are the same when aligned for maximum correspondence over the length of the nucleotide or amino acid sequence.

The "percentage of sequence identity" between two sequences is calculated by comparing two optimally aligned sequences over a comparison window, determining the number of positions at which the identical nucleotide or amino acid occurs in both sequences to yield the number of matched positions, dividing the number of matched positions by the total number of positions in the window of comparison (i.e., the window size), and multiplying the result by 100 to yield the percentage of sequence identity.

When percentage of sequence identity is used in reference to polypeptides it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers & Miller, *Computer Applic. Biol. Sci.*, 4: 11–17 (1988); Smith & Waterman, *Adv. Appl. Math.* 2: 482 (1981); Needleman & Wunsch, *J. Mol. Biol.* 48: 443 (1970); Pearson & Lipman, *Proc. Natl. Acad. Sci. USA* 85: 2444 (1988); Higgins & Sharp *Gene*, 73: 237–244 (1988); Higgins & Sharp, CABIOS 5: 151–153 (1989); Corpet et al., *Nucleic Acids Research* 16: 10881–90 (1988); Huang et al., *Computer Applications in the Biosciences* 8: 155–65 (1992); and Pearson et al., *Methods in Molecular Biology* 24: 307–31 (1994). Alignment is also often performed by inspection and manual alignment.

A subject nucleotide sequence or amino acid sequence is "substantially identical" to a reference sequence if the subject amino acid sequence or nucleotide sequence has at least 80% sequence identity over a comparison window. Thus, sequences that have at least 85% sequence identity, at least 90% sequence identity, at least 95% sequence identity or at least 99% sequence identity with the reference sequence are also substantially identical. Two sequences that are identical to each other are, of course, also substantially identical.

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotides of the first polynucleotide have the sequence of the nucleotides in the polynucleotide binding partner of the second polynucleotide. Thus, the polynucleotide whose sequence 5'-TATAC-3' is complementary to a polynucleotide whose sequence is 5'-GTATA-3'.

A nucleotide sequence is "substantially complementary" to a reference nucleotide sequence if the sequence complementary to the subject nucleotide sequence is substantially identical to the reference nucleotide sequence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA, mRNA and other RNA molecules such as hTR) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Recombinant" refers to polynucleotides synthesized or otherwise manipulated in vitro ("recombinant polynucleotides") and to methods of using recombinant polynucleotides to produce gene products encoded by those polynucleotides in cells or other biological systems. For example, an amplified or assembled product polynucleotide may be inserted into a suitable DNA vector, such as a bacterial plasmid, and the plasmid can be used to transform a suitable host cell. A host cell that comprises the recombinant polynucleotide is referred to as a "recombinant host cell". The gene is then expressed in the recombinant host cell to produce, e.g., a "recombinant protein." A recombinant polynucleotide may serve a non-coding function (e.g., promoter, origin of replication, ribosome-binding site, etc.) as well.

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences*, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, or intravenous intraperitoneal injection; or topical, transdermal, or transmucosal administration).

"Specifically binds to" refers to the ability of one molecule, typically a molecule such as an antibody or polynucleotide, to contact and associate with another specific molecule even in the presence of many other diverse molecules. For example, a single-stranded polynucleotide can "specifically bind to" a single-stranded polynucleotide that is complementary in sequence, and an antibody "specifically binds to" or "is specifically immunoreactive with" its corresponding antigen. Thus, under designated immunoassay conditions, an antibody binds preferentially to a particular protein and not in a significant amount to other proteins present in the sample. Specific binding to a protein under such conditions requires an antibody selected for its specificity for a particular protein. To select antibodies specifically immunoreactive with a particular protein, one can employ a variety of means, i.e., solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988).

A polynucleotide "specifically hybridizes" to a target polynucleotide if the polynucleotide hybridizes to the target under stringent conditions. "Stringent conditions" refers to temperature and ionic conditions used in nucleic acid hybridization. Stringent conditions depend upon the various components present during hybridization. Generally, stringent conditions are selected to be about 10° C., and preferably about 5° C. lower than the thermal melting point ($T_m$) for the specific sequence at a defined ionic strength and pH. The $T_m$ is the temperature (under defined ionic strength and pH) at which 50% of a target sequence hybridizes to a complementary polynucleotide.

A first sequence is an "antisense sequence" with respect to a second sequence if a polynucleotide whose sequence is the first sequence specifically hybridizes with a polynucleotide whose sequence is the second sequence.

"Substantially pure" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80 to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition.

"Suitable reaction conditions" are those conditions suitable for conducting a specified reaction using commercially available reagents. Such conditions are known or readily established by those of skill in the art for a variety of reactions. For example, suitable polymerase chain reaction (PCR) conditions include those conditions specified in U.S. Pat. Nos. 4,683,202; 4,683,195; 4,800,159; and 4,965,188. As one example and not to limit the invention, suitable reaction conditions can comprise: 0.2 mM each dNTP, 2.2 mM $MgCl_2$, 50 mM KCl, 10 mM Tris-HCl, pH 9.0, and 0.1% Triton X-100.

"Telomerase" or "telomerase ribonucleoprotein" refers to a ribonucleoprotein enzyme of eukaryotic origin identifiable by its ability to polymerize a DNA sequence of a eukaryotic telomere. Telomerase is further characterized by an RNA component having sequences complementary to at least part of the telomeric repeat of the source species and by one or more protein components. As used herein, "mammalian telomerase" and "human telomerase" refer to telomerases that can be found naturally in various mammalian or human cells, respectively, or having polypeptide components with the same amino acid sequences, and RNA components with the same nucleotide sequences. Human telomerase contains the RNA component, "hTR." The term "telomerase" includes all allelic forms of telomerase, including wild-type and mutant forms.

"Telomerase activity" refers to the synthesis of telomeric DNA by telomerase. A preferred assay method for detecting telomerase activity is the TRAP assay. See International Application published under the PCT, WO 95/13381. This assay measures the amount of radioactive nucleotides incorporated into elongation products, polynucleotides, formed by nucleotide addition to a telomerase substrate or primer. The radioactivity incorporated can be measured as a function of the intensity of a band on a PhosphorImager™ screen exposed to a gel on which the radioactive products are separated. A test experiment and a control experiment can be compared by visually using the PhosphorImager™ screens. See also the commercially available TRAP-eze™ telomerase assay kit (Oncor); and Morin, *Cell* 59: 521–529 (1989).

"Telomerase-related condition" refers to a condition in a subject maintained by telomerase activity within cells of the individual. Telomerase-related conditions include, e.g., cancer (telomerase-activity in malignant cells), fertility (telomerase activity in germ-line cells) and hematopoiesis (telomerase activity in hematopoietic stem cells).

"Accessible region of the RNA component of telomerase" refers to a region of an RNA component of telomerase (e.g., hTR) to which an antisense polynucleotide can specifically hybridize when the RNA component is part of the telomerase ribonucleoprotein.

The "template region" of the RNA component of mammalian telomerase refers to a subsequence of the RNA component of mammalian telomerase that serves as a template for synthesis of telomeric repeats. All vertebrates appear to have the conserved sequence 5'-TTAGGG-3' at chromosome ends, although subtelomeric sequences can vary (See, e.g., Harley & Villeponteau, Current Opin. in Gen. and Dev. 5: 249–255 (1995)). The template region is complementary to at least the single telomeric repeat sequence, and can also include a second portion of the telomeric repeat sequence. For example, the template region of hTR is 5'-CTAACCCTAA-3', located at nucleotides 46–55 of hTR (311–320 on SEQ ID NO:1).

"Primer" refers to a polynucleotide that is capable of specifically hybridizing to a complementary polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a complementary sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as radioactivity, that can be used to quantitate the amount of bound detectable moiety. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavidin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavidin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

"Amplification" refers to any means by which a polynucleotide sequence is copied and thus expanded into a larger number of polynucleotide molecules, e.g., by reverse transcription, polymerase chain reaction, and ligase chain reaction.

"Prognostic value" refers to an amount of the RNA component of telomerase detected in a given cancerous cell type that is consistent with a particular prognosis for the cancer. The amount (including a zero amount) of RNA component of telomerase detected in a sample is compared to the prognostic value for the cell such that the relative comparison of the values indicates the likely outcome of the cancer's progression.

"Diagnostic value" refers to a value that is determined for the RNA component of telomerase detected in a sample, which is then compared to a normal range of the RNA component of telomerase in a cell such that the relative comparison of the values provides a reference value for diagnosing cancer. Depending upon the method of detection, the diagnostic value may be a determination of the amount of the RNA component of telomerase in a sample, but it is not necessarily an amount. The diagnostic value may also be a relative value, such as a plus or a minus score, and also includes a value indicating the absence of the RNA component of telomerase in a sample.

II. THE RNA COMPONENT OF TELOMERASE

Human genomic DNA encoding hTR has been cloned, sequenced and placed on deposit. A lambda clone designated "28-1" contains an ~15 kb insert containing human telomerase RNA component gene sequences. Clone 28-1 was deposited with the American Type Culture Collection pursuant to the Budapest Treaty and granted accession number ATCC 75925. Plasmid pGRN33 contains an ~2.5 kb HindIII-SacI insert containing sequences from lambda clone 28-1 that contain the sequence of hTR. Plasmid pGRN33 was deposited with the American Type Culture Collection pursuant to the Budapest Treaty and granted accession number ATCC 75926. A PstI fragment of the ~2.4 kb SauIIIA1-HindIII fragment of clone 28-1 also contains the hTR sequence. The sequence of the PstI fragment is provided in SEQ ID NO:1, below. The nucleotides of hTR are indicated above the sequence indicated by stars and numbered 1 to 451. The template region is underlined.

III. METHODS OF DETECTING THE RNA COMPONENT OF TELOMERASE

The method of detecting the presence, absence or amount of the RNA component of telomerase in a sample involves two steps: (1) specifically hybridizing a polynucleotide to an accessible region of the RNA component of telomerase, and (2) detecting the specific hybridization. Detection refers to determining the presence, absence, or amount of the RNA component of telomerase in a sample, and can include quantitation of the amount of RNA component of telomerase per cell in a sample.

For the first step of the method, the polynucleotide used for specific hybridization is chosen to hybridize to any suitable region of the RNA component of telomerase. In one embodiment, the region is an accessible region, excluding the template region. Such polynucleotides allow efficient detection of hTR in cell extracts and tissue samples, as described herein. The polynucleotide can be a DNA or RNA molecule, as well as a synthetic, non-naturally occurring analog of the same. The polynucleotides in this step are polynucleotide primers and polynucleotide probes. Suitable primer lengths are from 7–50 nucleotides, preferably from 10–40 nucleotides, and most preferably from 15–35 nucleotides. Specific hybridization conditions are selected by those skilled in the art, as discussed herein.

For the second step of the reaction, any suitable method of detecting specific hybridization of a polynucleotide to the RNA component of telomerase may be used. Such methods include, e.g., amplification by extension of a hybridized primer using reverse transcriptase (RT); extension of a hybridized primer using RT-PCR or other methods of amplification; and in situ detection of a hybridized primer (see, e.g., U.S. patent application Ser. No. 08/482,115, filed Jun. 7, 1995). Detectable moieties used in these methods include, e.g., labeled polynucleotide probes; direct incorporation of label in amplification or RT reactions, and labeled polynucleotide primers.

A. Reverse Transcription

A first method for detecting specific hybridization of a polynucleotide to the RNA component of telomerase is reverse transcription. Reverse transcription is an amplification method that copies RNA into DNA. The reverse transcription reaction, which synthesizes first strand cDNA, is performed by mixing RNA with random hexamer primer or a specific primer, heating to 95° C. for 5 minutes to denature the nucleic acids (the thermal cycler may be used for this step), and then cooling on ice. The reaction mixture, prepared according to the enzyme manufacturers instructions or according to kit instructions, is added to the denatured RNA and hexamer mixture and incubated at a suitable temperature, usually 42° C. The reaction is stopped by heating the tube containing the reaction mixture for 10 minutes at 95° C. The first strand cDNA is collected by precipitation and brief centrifugation and aliquoted to new tubes, in which it can be quickly frozen on dry ice and stored at −80° C., if necessary, for later use.

B. RT-PCR

Methods of amplification reactions, e.g., PCR (polymerase chain reaction) or LCR (ligase chain reaction) are known in the art (PCR Technology. Principles and Applications for DNA Amplification (Erlich, ed., 1989); PCR Protocols: A Guide to Methods and Applications (Innis, Gelfland, Sninsky, & White, eds., 1990); Mattila et al., Nucleic Acids Res. 19: 4967 (1991); Eckert & Kunkel, PCR Methods and Applications 1: 17 (1991); and the U.S. Patents referenced above). Optimal reverse transcription, hybridization, and amplification conditions will vary depending upon the sequence composition and length(s) of the targeting polynucleotide(s) primers and target(s) employed, and the experimental method selected by the practitioner. Various guidelines may be used to select appropriate primer sequences and hybridization conditions (see, e.g., Sambrook et al., supra).

PCR is typically carried out in a buffered aqueous solution, preferably at a pH of 7–9. Deoxyribonucleoside triphosphates are added to the synthesis mixture in adequate amounts, and the resulting solution may be heated to about 85°–100° C. for about 1 to 10 minutes. After this optional heating period, the solution is allowed to cool to about 20°–40° C., for primer hybridization. An agent for polymerization is added to the mixture, and the reaction is allowed to occur under conditions known in the art, typically using a thermocycler. This synthesis reaction may occur at room temperature up to a temperature just over which the agent for polymerization no longer functions efficiently. The agent for polymerization may be any compound or system that will function to accomplish the synthesis of primer extension products, including enzymes. Suitable enzymes for this purpose include, for example, E. coli DNA polymerase I or Klenow fragment, Taq DNA polymerase, and other available DNA polymerases. A preferred embodiment of detection uses an RT-PCR protocol, as described in Example 1. RT-PCR combines reverse transcription of RNA into DNA and subsequent DNA amplification reactions in a single reaction.

C. In Situ Hybridization

Identification of cells, typically in a mixed population, that express the RNA component of telomerase can be performed by in situ hybridization. A sample of tissue or cells is fixed onto a glass slide and permeablized sufficiently for use with in situ hybridization techniques, according to standard methods. After the sample is fixed, a primer that specifically hybridizes to the RNA component of telomerase is hybridized to the sample, and then the hybridization of the primer is detected, for example, using an RT-PCR protocol or other methods described herein.

D. Detectable Moieties

These methods of detecting hybridization, described above, generally include the use of a detectable moiety. Primers and probes that include detectable moieties are synthesized by standard methods known to those skilled in the art (see Ausubel, et al., and Sambrook, et al., supra). The detectable moiety may be directly or indirectly detectable and associated with either a primer or a probe. Directly detectable moieties include, e.g., polynucleotides that are labeled with $^{32}$P at the 5' end of the molecule (see Example 1), or that incorporate radioactive nucleotides. Indirectly detectable moieties include, for example, polynucleotides that incorporate biotinylated nucleotides recognized by streptavadin, or a nucleotide sequence, which is the binding partner for a radioactively labeled complementary sequence.

The detectable moiety often generates a measurable signal, such as a radioactive, chromogenic, or fluorescent signal, that can be used to quantitate the amount of bound detectable moiety, for example, for determination of a diagnostic value or a prognostic value for hTR in a sample. Quantitation of the signal is achieved by methods known to those skilled in the art, for example, scintillation counting, densitometry, or flow cytometry. Determination of such a diagnostic value or a prognostic value allows comparison with a value for hTR in a normal cell sample. Using this comparison, a diagnosis or prognosis regarding the patient's sample may be determined.

IV. CO-AMPLIFICATION

Often, cell extracts or tissue samples used in methods of determining the amount of the RNA component of telomerase in a sample will contain variable amounts of cells or extraneous extracellular matrix materials. In addition, the amplification efficiency may vary from reaction to reaction. Thus, a method of determining the cell number in a sample is important for determining the relative amount per cell of a test polynucleotide such as hTR. In addition, a method of determining amplification efficiency is important for determining the relative amount of hTR in a sample. A control for cell number and amplification efficiency is useful for determining diagnostic values for a sample of a potential cancer, and a control is particularly useful for comparing the amount of test polynucleotide such as hTR in sample to a prognostic value for a cancer. Previous work has used 28S rRNA as a control, by diluting reverse transcribed 28S rRNA and adding it to the amplification reaction (Khan et al., *Neurosci. Lett.* 147: 114–117 (1992)).

This invention thus provides a method of quantitation of the amount in a sample of a test polynucleotide, for example, hTR, involving co-amplification of the test polynucleotide with a control polynucleotide in an RT-PCR reaction. Two or more polynucleotides may be co-amplified in a single sample. This method is a convenient method of quantitating the amount of hTR in a sample, because the RT and amplification reactions are carried out in the same reaction for a test and control polynucleotide. The co-amplification of the control polynucleotide allows normalization of the cell number in the sample as compared to the amount of hTR in the sample. This feature is particularly useful for diagnostic and prognostic methods for cancers because these values must be correlated with standard diagnostic and prognostic values for various cancers. Co-amplification with an internal control can also provide a standard for amplification efficiency.

Suitable control polynucleotides for co-amplification reactions include DNA, RNA expressed from housekeeping genes, constitutively expressed genes, and in vitro synthesized RNAs added to the reaction mixture. Endogenous control polynucleotides are those that are already present in the sample, while exogenous control polynucleotides are added to a sample, creating a "spiked" reaction. Suitable controls include, e.g., β-actin RNA, GAPDH RNA, "SnRNP" RNA (RNA components of snRNPs), ribosomal RNA, and satellite DNA. A preferred embodiment of the control RNA is endogenously expressed 28S rRNA.

The control and test polynucleotides will often differ in their abundance in a cell. For the co-amplification method to be useful for quantitation, the control and test polynucleotides must both be amplified in a linear range. The co-amplification reaction can be performed using an endogenous or exogenous control polynucleotide that is equally, more, or less abundant than the test polynucleotide. In a preferred embodiment, the control polynucleotide is more abundant than hTR, for example, 28S rRNA is about 10,000 times more abundant than hTR in cells.

To achieve linear amplification of both control and test polynucleotides in the same reaction when one target is considerably more abundant than the other, the primers for the more abundant target, such as 28S rRNA, can be designed so that they are less efficient for amplification. For example, the primers can contain mismatches at the 5' end so that reverse transcription of the control polynucleotide is less efficient due to less efficient primer hybridization, and thus less efficient extension by RT. Another method of achieving less efficient hybridization is to create shorter control primers, which are less efficient both at the RT and at the amplification step. If the test polynucleotide is more abundant than the control, then primers are designed for the test polynucleotide so that so that the amplification of the test polynucleotide is less efficient, as described above. Both of these methods can be used for the same primer, creating a control primer set that is about 10,000 fold less efficient both at the RT and the PCR steps.

The co-amplification method is typically carried out using an RT-PCR protocol, which can be performed according to methods known to those skilled in the art, and for which kits are commercially available. Test cell or patient samples are obtained from convenient sources such as CHAPS cell extracts or total RNA (see Example 1). The initial reverse transcription reaction uses specific primers, as described herein, that can include mismatches at the 5' end to provide less efficient priming of the control primers. After the RT reaction, the subsequent PCR reaction occurs in the same tube, using the same oligonucleotides. The control cDNA can also be amplified in a less efficient manner by using relatively short control primers (as compared to the hTR primers). Embodiments of control primers include SEQ ID NOS:15–24, with SEQ ID NOS:19 and 23 as preferred embodiments. Embodiments of hTR primers include SEQ ID NOS:25 and 26 (see, e.g., Table I, which lists control and test polynucleotides). Other suitable primers, which can also contain mismatches at the 5' end and relatively shorter lengths, can be determined by one skilled in the art. The primers for the RNA component of telomerase may be directed toward any convenient region of the sequence. For example, primers can be chosen that specifically hybridize to accessible regions of hTR, such as nucleotides positions 137–196, 290–319, and 350–380 of hTR (see SEQ ID NO:1 and FIG. 1).

The RT-PCR products can be analyzed by polyacrylamide gel electrophoresis and visualization of the products, e.g., by autoradiography or fluorescence. RT-PCR co-amplification can also be carried out on tissue samples prepared for in situ hybridization, and the product visualized using a microscope. The in situ hybridized samples can also be quantitated using, for example, by counting the fluorescent, radioactive, or chromogenic signal. After determining the amounts of the RNA component of telomerase in a sample, and the amounts of endogenous control in a sample, the amount of the RNA component of telomerase is normalized per cell, using the following formula: signal of test nucleic acid divided by signal of control nucleic acid. This normalized value is useful either as a diagnostic value, to be compared with the normalized amount of the RNA component in a normal sample, or an amount to be compared with a normalized prognostic value. When exogenous internal controls are used in the co-amplification reaction, amplification efficiency can also be normalized as well as the amount of hTR per cell using the following formula: signal of test nucleic acid (hTR)/signal of internal control (hTR-IC) divided by signal of control nucleic acid (rRNA)/signal of internal control.(28S rRNA-IC)

V. POLYNUCLEOTIDE PROBES AND PRIMERS

The methods of the invention involve the use of polynucleotides that specifically hybridize to sequences of the RNA component of telomerase in a sample. The polynucleotide probes and primers used in the invention have the ability to specifically hybridize to a subsequence of the RNA component of telomerase or its complement under the conditions used in the particular method of detection. Probes or primers that can specifically hybridize to, for example, the sequence of hTR described above, are used in the invention. One embodiment of oligonucleotides that can hybridize to hTR is described in Example 1 (SEQ ID NO:25 and SEQ ID NO:26). Polynucleotide primers and probes that specifically hybridize to the RNA component of mammalian telomerase are also described in U.S. Pat. No. 5,583,016; U.S. patent application Ser. No: 08/272,102, filed Jul. 7, 1994; U.S. Ser. No. 08/472,802, filed Jun. 7, 1995; U.S. Ser. No. 08/482, 115, filed Jun. 7, 1995; U.S. Ser. No. 08/521,634, filed Aug. 31, 1995; U.S. Ser. No. 08/630,019, filed Apr. 9, 1996; U.S. Ser. No. 08/660,678, filed Jun. 5, 1996; and International Application PCT/US95/08530, filed Jul. 6, 1995.

Any suitable region of the RNA component of telomerase may be chosen as a target for polynucleotide hybridization. A detectable moiety bound to either an oligonucleotide primer or a probe is subsequently used to detect hybridization of an oligonucleotide primer to the RNA component. Detection of labeled material bound to the RNA component of telomerase in a sample provides a means of determining a diagnostic or prognostic value (see section V., below). The methods of the invention are also useful in detecting the presence, absence or amount of hTR in tissue biopsies and histological sections where the detection method is carried out in situ, typically after amplification of hTR using a primer set.

In particular, regions of hTR that are accessible in the native telomerase ribonucleoprotein have been identified and are useful for detecting the presence, absence, or amount of hTR. The regions were identified in two ways. The first way involved contacting samples containing human telomerase with a variety of DNA polynucleotides having sequences complementary to the sequence of hTR under hybridization conditions, contacting the telomerase with RNase H, which cleaves the RNA strand of an RNA-DNA duplex, and determining whether hTR had been cleaved. Antisense oligonucleotides that supported hTR cleavage were complementary to nucleotides 137–196, 290–319 and 350–380 of hTR (see, e.g., sequences listed in Table II and FIG. 1). Specific polynucleotides capable of supporting RNase H cleavage are described in more detail in Example 2. The second way involved oligo-decoration. This method indicated that nucleotides 167–193 also are accessible. Regions of hTR accessible in the telomerase ribonucleoprotein comprise these areas. Other accessible areas of hTR can be identified by similar assays using antisense polynucleotides whose sequences are substantially complementary to a nucleotide sequence selected from hTR. The RNA component of telomerase of other mammals also contains accessible regions in the telomerase ribonucleoprotein. Accessible regions of the RNA component of telomerase and their uses are also described in U.S. patent application Ser. No. 08/770,564, filed Dec. 20, 1996 (Kealy et al., "Inhibitory Polynucleotides Directed Against the RNA Component of Telomerase," Geron docket no. 014).

The conditions required for specific hybridization of polynucleotide probes and primers vary according to the sequence and length of the primer or probe, and the reaction conditions of the hybridization reaction. Determination of the conditions for specific hybridization are known by those skilled in the art (see Sambrook et al., *Molecular Cloning. A Laboratory Manual* (2d ed. 1989); Ausubel et al., *Current Protocols in Molecular Biology* (1995)). In one embodiment, the conditions for hybridization are those described in Examples 1 and 2. Nucleotide substitutions, deletions, and additions may be incorporated into the polynucleotides used in the invention, as long as the characteristic ability to specifically hybridize to the target hTR sequence or its complement is retained. Nucleotide sequence variation may result from sequence polymorphisms of various alleles, minor sequencing errors, and the like.

Although primers and probes can differ in sequence and length, the primary differentiating factor is one of function: primers serve as an initiation point for DNA synthesis of a target nucleic acid, as in RT and PCR reactions, while probes are typically used for hybridization to and detection of a target nucleic acid. Typical lengths of primers or probes can range from 7 to 50 or more nucleotides. A primer or probe can also be labeled with a detectable moiety for detection of hybridization of the primer or probe to the target hTR nucleic acid.

As a general point regarding the nucleic acids used in the invention, those of skill in the art recognize that the nucleic acids used in the invention include both DNA and RNA molecules and naturally occurring modifications thereof, as well as synthetic, non-naturally occurring analogs of the same, and heteropolymers, of deoxyribonucleotides, ribonucleotides, and/or analogues of either. The particular composition of a nucleic acid or nucleic acid analog will depend upon the purpose for which the material will be used and the environment in which the material will be placed. Modified or synthetic, non-naturally occurring nucleotides have been designed to serve a variety of purposes and to remain stable in a variety of environments, such as those in which nucleases are present, as is well know in the art. Modified or synthetic non-naturally occurring nucleotides, as compared to naturally occurring ribo- or deoxyribonucleotides may differ with respect to the carbohydrate (sugar), phosphate bond, or base portions of the nucleotide, or may even contain a non-nucleotide base (or no base at all) in some cases (see, e.g., Arnold et al., PCT patent publication no. WO 89/02439). For example, the modified or non-naturally occurring nucleic acids of the invention can include biotinylated nucleic acids, phosphorothioates, phosphoramidates, methyl phosphonates, chiral-methyl phosphonates, 2-O-methyl ribonucleotides and peptide-nucleic acids (See, e.g., U.S. Pat. Nos: 5,506,212, 5,521,302, 5,541,307, and 5,510,476).

Oligonucleotides preferably are synthesized on an Applied BioSystems or other commercially available oligonucleotide synthesizer according to specifications provided by the manufacturer. Oligonucleotides may be prepared using any suitable method, such as the phosphotriester and phosphodiester methods, or automated embodiments thereof. In one such automated embodiment, diethylphosphoramidites are used as starting materials and may be synthesized as described by Beaucage et al., *Tetrahedron Letters* 22: 1859 (1981), and U.S. Pat. No. 4,458,066.

Nucleic acids, e.g., probes, also can be recombinantly produced through the use of plasmids or other vectors. Accordingly, this invention also provides vectors, i.e., recombinant nucleic acid molecules comprising expression control sequences operatively linked to a nucleotide sequence encoding a region of the RNA component of telomerase.

Vectors can be adapted for function in prokaryotes or eukaryotes by inclusion of appropriate promoters, replication sequences, selectable markers, etc. for replication and transcription of a nucleotide sequence. The construction of vectors and the replication and expression of genes in transfected cells involves the use of molecular cloning techniques also well known in the art (see, e.g., Ausubel et al., supra; Sambrook et al., supra; Berger & Kimmel, volume 52, *Methods in Enzymology, Guide to Molecular Cloning Techniques* (1987)). The particular vector used to transport the genetic information into the cell is also not particularly critical. The vector containing the sequence of interest is transformed into host cells for replication and expression. The particular procedure used to introduce the genetic material into the host cell is not particularly critical. It is only necessary that the particular procedure utilized be capable of successfully introducing at least one gene into the host cell which is capable of expressing the gene (see generally Sambrook et al., supra; Ausubel, et al., supra.

VI. DIAGNOSIS AND PROGNOSIS OF CANCER

Methods of determining whether a sample contains the RNA component of telomerase, and the amount of the RNA component, are particularly useful for diagnosis of cancer and determining its prognosis. In the diagnostic and prognostic methods of the invention, the assay is conducted to determine whether the RNA component of mammalian telomerase is present, whether the diagnostic value of the sample is higher than the value in a normal range of cells, and how the amount of the RNA component of telomerase in a sample compares to a prognostic value. The cells used to determine the normal range of RNA component expression can be normal cells from the individual to be tested, or normal cells from other individuals not suffering from a disease condition. The determination of a diagnostic value of the RNA component of mammalian telomerase above normal range is indicative of the presence of immortal cells, such as certain types of cancer cells, and these values can be used to aid or make a diagnosis even when the cells would be classified as non-cancerous by pathology. Comparison of the amount of the RNA component of mammalian telomerase with a prognostic value for a given cancerous cell type allows staging of the cancer and determination of a prognosis. Thus, the methods of the present invention allows cancerous conditions to be detected with increased confidence and possibly at an earlier stage, before cells are detected as cancerous based on pathological characteristics.

The diagnostic and prognostic methods of the present invention can be employed with any cell or tissue type of any origin and can be used to detect an immortal or neoplastic cell, or tumor tissue, or cancer, of any origin, provided the cell expresses telomerase activity and therefore its RNA component. For patient samples (referring to a sample for hTR detection), the detection of immortal cells will typically be used to detect the presence of cancer cells of any of a wide variety of types, including solid tumors and leukemias. Types of cancer that may be detected include, for example, adenocarcinoma of the breast, prostate, and colon; all forms of bronchogenic carcinoma of the lung; leukemias such as mixed cell, T-cell chronic, lymphocytic acute, lymphocytic chronic, and myeloid; Hodgkin's disease; melanoma; hepatoma; neuroblastoma; and papilloma. Typically, in situ hybridization assays will be used for heterogenous or focal diseases such as breast and prostate cancer, while tube-based solution assays will be used for homogenous tumors such as neuroblastoma. In particular, the co-amplification method of the invention is useful for diagnostic and prognostic assays because it provides a method of determining the amount of hTR per cell. The quantitation allows comparison of patient sample values with standard prognostic and diagnostic values. In addition, quantitation via co-amplification is useful for determining the amount of hTR per cell in samples that contain extracellular materials.

The diagnostic and prognostic methods can also be carried out in conjunction with other diagnostic or prognostic tests. In some instances, such combination tests can provide useful information regarding the progression of a disease, although the present methods of testing for hTR provide much useful information in this regard. When the present methods are used to detect the presence of cancer cells in patient's sample, the presence of hTR can be used to determine the stage of the disease, whether a particular tumor is likely to invade adjoining tissue or metastasize to a distant location, and whether a recurrence of the cancer is likely. Tests that may provide additional information include diagnostic tests for the estrogen receptor, progesterone receptor, DNA ploidy, fraction of cells in S-phase, nodal status, and presence of oncogene gene products.

Those of skill in the art will also recognize that a variety of patient samples can be used in the methods of the invention. For example, cell extracts, cultured cells, or tissue samples provide convenient samples for use with the methods of the invention. The methods of the invention can use samples either in solution or extracts, for example, with RT-PCR, or samples such as tissue sections for in situ methods of detection. Samples can also be obtained from sources such as cells collected from bodily fluids and wastes, e.g., urine, sputum, and blood; washes, e.g., bladder and lung; and fine-needle biopsies, e.g., from prostate, breast, and thyroid; cellular materials; whole cells; tissue and cell extracts; RNA extracted from tissue and cells; and histological sections of tissue.

The diagnostic and prognostic methods of the invention are carried out using methods of detecting the presence, absence or amount of the RNA component of mammalian telomerase, as described herein. A suitable cell sample is contacted with a polynucleotide that can specifically hybridize to the RNA component of mammalian telomerase, e.g., polynucleotides to accessible regions of hTR, and then the hybridization is detected using any of the methods described above. One embodiment of this method uses an RT-PCR protocol, and a preferred embodiment of the method uses co-amplification of hTR and a control RNA to provide a means of quantitation.

The present invention also provides for kits for performing the diagnostic and prognostic method of the invention. Such kits can be prepared from readily available materials and reagents. For example, such kits can comprise any one or more of the following materials: enzymes, reaction tubes, buffers, detergent, primers and probes that target hTR, primers and probes that target a control RNA such as 28S rRNA, control reagents, and instructions. A wide variety of kits and components can be prepared according to the present invention, depending upon the intended user of the kit and the particular needs of the user. One such kit can include primers for RT-PCR of hTR, and/or in situ detection of hTR in a sample. In one embodiment, the kit includes oligonucleotide primers that are directed to an accessible region of hTR. A preferred kit includes primers for co-amplification of hTR with a set of control primers such as 28S rRNA.

EXAMPLES

Example 1

RT-PCR Co-Amplification of hTR

The following example is provided by way of illustration only and not by way of limitation. Those of skill will readily recognize a variety of noncritical parameter that could be changed or modified to yield essentially similar results.

hTR was co-amplified in an RT-PCR reaction with an internal control. This method is particularly useful for prognostic and diagnostic methods of hTR detection because it provides an accurate and efficient method of quantitation of the amount of hTR per cell in a sample. In the first experiment, endogenous 28S rRNA was the control polynucleotide co-amplified with hTR. In the second experiment, 28S rRNA and hTR were amplified in separate tubes, with each RT-PCR reaction containing a corresponding in vitro synthesized internal control. The following primers were used in the RT-PCR co-amplification reaction:

TABLE I 28S rRNA primers:

| | |
|---|---|
| Forward: | GCT AAA TAC CGG CAC GAG ACC GAT AG (SEQ ID NO:15) |
| | GCT AAA TAC CGG CAC GAG AC (SEQ ID NO:16) |
| | GCT AAA TAC CGG CAC GAG (SEQ ID NO:17) |
| | GAT CTA AAT ACC GGC ACG (SEQ ID NO:18) |
| | GAG CTA AAT ACC GGC ACG (SEQ ID NO:19) |
| Reverse: | GGT TTC ACG CCC TCT TGA ACT CTC TC (SEQ ID NO:20) |
| | GTT TCA CGC CCT CTT GAA CTC (SEQ ID NO:21) |
| | GTT TCA CGC CCT CTT GAA C (SEQ ID NO:22) |
| | CTA GTT TCA CGC CCT CTT G (SEQ ID NO:23) |
| | CTG GTT TCA CGC CCT CTT G (SEQ ID NO:24) | hTR primers:

| | |
|---|---|
| Forward: | GAA GGG CGT AGG CGC CGT GCT TTT GC (SEQ ID NO:25) |
| Reverse: | GTT TGC TCT AGA ATG AAC GGT GGA AGG (SEQ ID NO:26) |

A. Co-amplification with Endogenous 28S rRNA

Co-amplification with an endogenous control, for which a copy number is known or for which a standard curve can be created, provides a means of determining the amount of hTR per cell in a sample. In this example, endognous 28S rRNA is used as a control in the RT-PCR co-amplification reaction.

Samples for the RT-PCR reaction were typically prepared by CHAPS extraction of cell samples, as described in Kim et al., Science 266: 2011–2015 (1994), or RNA can be isolated by any standard method known to those skilled in the art. Cell types used for CHAPS extraction and co-amplification reactions include: HeLa, MCF7, 293, HT1080, EJ, and IMR90 (the latter two cell types are normal cells, the remainder are immortal or cancer cells). For CHAPS extract samples, 1 µl of 1 µg/µl total protein was used per reaction, or for isolated RNA samples, 1 µl of 1 µg/µl total RNA was used per reaction.

CHAPS extract samples were heat denatured for at least 5 minutes at 95° C. before the RT-PCR reaction was initiated. This denaturation step may be combined with the RT-PCR cycling step. As a control for genomic DNA contamination, 10 units of RNase per sample was added to selected samples, incubated for at least 10 minutes at 37° C., and then denatured for 10 minutes at 95° C.

The RT-PCR reactions (25 µl) with CHAPS extracted samples were assembled as follows using the EZ rTth RNA PCR kit (Perkin Elmer): 7 µl water, 5 µl 5×EZ buffer, 3 µl 2.5 µM dNTPs, 2 µl 25 µM Mn(OAc)$_2$, 1 µl rTth DNA polymerase, 1.5 µl each reverse primer (20 µM stock solution) (hTR and 28S rRNA primers), and 2 µl each forward primer (20 µM stock solution) (hTR and 28S rRNA primers).

The RT-PCR reaction described above was incubated in a thermocycler using the following conditions: (1) 1 cycle at 94° C. for 5 minutes, (2) 1 cycle at 65° C. for 30 minutes (RT reaction), (3) 1 cycle at 94° for 1.5 minutes, and (4) 30 cycles of the following sequence: 94° C. for 0.5 minute then 65° C. for 1 minute followed by 72° C. for 7 minutes. Reaction conditions may be adjusted according to the type of sample used, e.g., CHAPS extract or total RNA.

Reaction products were typically analyzed by gel electrophoresis, using a 12.5% polyacrylamide, 1× TBE gel. The reaction was also performed with one primer from each pair labeled with $^{32}$P at the 5' end Using γ$^{32}$P-ATP, according to standard reaction conditions (see, e.g., Sambrook et al., supra). The amplification products were then detected by gel electrophoresis followed by autoradiography. Other standard methods of labeling and types of labels may be used, for example, biotinylated labels, or staining with DNA dyes such as ethidium bromide or SYBR Green. If unlabeled primers are used, the amplification products may be detected by gel electrophoresis, blotting, and hybridization with a labeled polynucleotide probe.

The ratio between hTR and control 28S rRNA amplification products may be determined by densitometry scanning of an autoradiogram, or by any other suitable method known to one skilled in the art, e.g., counting radioactivity, fluorescence or chromogenicity. The following formula was used to normalize the amount of hTR in a cell: signal of test nucleic acid (hTR) divided by signal of control nucleic acid (rRNA). The amount of hTR per sample according to this formula was used to determine diagnostic and prognostic values for a sample, and to determine the amount of hTR per cell.

This experiment yielded the following results: The amplification efficiency of 28S rRNA was reduced by mismatches and shortened length introduced into the primer sets. The reduction of 28S rRNA amplification efficiency allowed co-amplification of hTR, which is present at approximately 10,000 fold lower levels than 28S rRNA. In titrated Hela extracts, the level of 28S rRNA and hTR co-amplified in the same reaction decrease linearly, demonstrating that the assay can be used to quantitate the amount of hTR per cell.

B. Co-amplification with In Vitro Synthesized Internal Controls

Co-amplification of hTR with an internal control, in parallel with co-amplification of 28S rRNA with an internal control, provides a means for determining amplification efficiency. In addition, amount of 28S rRNA in the sample can be compared to a standard curve for that sample type, thus allowing a determination of the amount of hTR in a sample. In this example, exogenous controls are added to the RT-PCR co-amplification reaction.

In a second experiment, the hTR and 28S rRNA co-amplification reactions were performed in separate tubes, with in vitro synthesized internal controls added to each reaction. The hTR reaction contained hTR-IC (hTR internal control transcript) and the 28S rRNA reaction contained 28S rRNA-IC (28S rRNA internal control transcript). The reactions were assembled as described herein, except that each reaction contained an in vitro synthesized internal control, and one primer set (hTR or 28S rRNA) instead of two primer sets (hTR and 28S rRNA).

The RNA internal controls were synthesized in vitro using an RNA Polymerase Kit (Stratagene), according to the manufacturer's instructions. The RNA internal controls were isolated from the synthesis reaction according to standard procedures, and the concentration of each internal control was determined. Typically, 1 μl of 0.2 μg/μl 28S rRNA-IC, and 1 μl of 4 ng/μl hTR-IC were added to each co-amplification reaction. These concentrations may be varied to determine the optimal concentration of the internal control.

The RT-PCR was assembled as described above except that 1 μl of internal control was added per RT-PCR co-amplification reaction and one primer set was added to the reaction. After the co-amplification reaction was complete, reaction products were analyzed as described above. The following formula was used to determine amplification efficiency and quantitate the amount of hTR RNA per cell: signal of test nucleic acid (hTR)/signal of internal control (hTR-IC) divided by signal of control nucleic acid (rRNA)/signal of internal control (28S rRNA-IC).

Example 2
Identification of Accessible Regions of hTR

A set of 17 contiguous antisense DNA oligonucleotides (30 mers) were tested for their ability to direct RNase H cleavage of hTR in the context of the native telomerase enzyme. Three antisense DNA 30 mers (denoted "14", "16", and "21") directed efficient cleavage of hTR, indicating that the corresponding regions of hTR were accessible to DNA probes in the intact ribonucleoprotein particle (RNP). Antisense oligonucleotides "14", "16", and "21" (see Table II) were tested as potential inhibitors of human telomerase ("hTase"). These regions corresponded to nucleotides 350–380, 290–319 and 137–166 of hTR.

Preincubation of partially purified nuclear or cytoplasmic extract with antisense oligonucleotide "21" (directed against nucleotides 137 to 166 of hTR) resulted in potent inhibition of hTase, as indicated by the standard primer elongation assay. Antisense oligonucleotides "14" and "16" and a "sense" oligonucleotide did not significantly affect hTase activity. A 20 mer antisense oligonucleotide comprised of 2'-o-methyl RNA directed against nucleotides 147 to 166 of hTR also inhibited hTase. The concentration of antisense oligonucleotide that yielded 50% hTase inhibition (IC50) was estimated from an activity versus antisense oligo concentration profile. The IC50s for the 20 mer and 30 mer antisense oligonucleotides were in the range of 1 to 10 nanomolar (antisense oligo:hTase at IC50=3:1). Control antisense oligonucleotide yielded no inhibition of hTase at oligo concentrations of 600 to 2000 nanomolar. Northern analysis showed that hTR remained intact throughout the inhibition protocol, suggesting the antisense inhibition of hTase was independent of RNase H activity.

The accessible regions were "fine mapped" by using shorter antisense oligonucleotides to direct RNase H cleavage of hTR. For the "14" region, a 20 mer (14ab) and a 12 mer (14d) directed RNase H cleavage. For the "16" region, two 20 mers (16ab, 16bc) directed RNase H cleavage. For the "21" regions, an antisense oligo as small as 7 nucleotides directed RNase H cleavage within the 147–166 region of hTR. Hence, these "short" antisense oligonucleotides might also inhibit hTase. A map summarizing antisense sequences able to direct RNase H cleavage of hTR in the native RNP is shown in FIG. 1.

TABLE II

| Oligo # | Sequence (SEQ ID NOS: 2–13) | RNaseH Digestion? | Capture? (2'OMe) | Activity on beads | NB ref GLN –21 |
| --- | --- | --- | --- | --- | --- |
| 14 | 5' CGT TCC TCT TCC TGC GGC CTG AAA CGG TGA 3' | yes | | | 73 |
| 14ab | 5' CGT TCC TCT TCC TGC G9C CT 3' | yes | yes | yes | 92 |
| 14bc | 5' CCT GCG GCC TGA AAC GGT GA 3' | no | NA | NA | 92 |
| 14d | 5' CGT TCC TCT TCC 3' | yes | yes | yes | 106 |
| 16 | 5' CTG ACA GAG CCC AAC TCT TCG CGG TGG CAG 3' | yes | | | 73 |
| 16ab | 5' CTG ACA GAG CCC AAC TCT TC 3' | yes | yes | no | 92 |
| 16bc | 5' CCA ACT CTT CGC GGT GGC AG 3' | yes | yes | NT | 92 |
| | 5' GCT CTA GAA TGA ACG GTG AAG GCG GCC AGG 3' | yes | | | 73, 13 |
| 21ab | 5' GCT CTA GAA TGA ACG GTG G 3' | yes | yes | * | 177 |
| 21ab3 | 5' GCT CTA GAA TGA ACG 3' | yes | NT | * | 177 |
| 21ab2 | 5' GCT CTA GAA TG 3' | yes | yes | NT | 177 |
| 21ab1 | 5' GCT CTA G 3' | yes | yes | yes | 177 |
| 20/21 | 5' CAT TTT TTG TTT GCT CTA GA 3' | yes | NT | NT | 177 |

NA = not applicable
NT = not tested
*known to inhibit telomerase

On the bases of the antisense data, biotinylated 2'OMe antisense RNA analogs were designed for affinity purification of telomerase. The goal of the antisense affinity approach was to design ligands that afforded good purification and yield, while keeping the enzyme intact (i.e., active). Several 2'OMe ligands met our criteria (Table II, FIG. 1). The biotinylated 2'Me analogs of 14ab and 14d, as well as the 21ab1 analog, "captured" active telomerase on streptavidin beads. These analogs were further refined via the synthesis of second generation antisense affinity ligands, which were designed to allow release of active telomerase (reversible ligands). Currently, our affinity scheme consists of two reversible antisense ligands, which are employed in series, and target two different regions of hTR. The first ligand is a disulfide version of 14ab which allows release of telomerase via dithiothreitol treatment. The second ligand contains the 21ab1 antisense sequence and plus a tail of "nonsense" sequence. hTR is released from the antisense ligand by a displacement DNA oligonucleotide, which is complementary to the entire length of the 21ab1 antisense affinity ligand.

Oligodecoration was used to further identify accessible regions of the telomerase ribonucleoprotein. Radioactively labeled 2 0-methyl antisense polynucleotides were prepared and exposed to the telomerase ribonucleoprotein. The sample was incubated to allow the polynucleotide to bind to telomerase. Then the sample was run on a native gel. Polynucleotides that had bound to telomerase exhibited altered mobility on the gel. In particular, polynucleotides RP2 and RP3 (FIG. 1) were found to bind to the telomerase ribonucleoprotein. RP2 has the sequence CGG GCC AGC AGC TGA CA (SEQ ID NO:14). This demonstrated that nucleotides 167–193 are accessible to antisense polynucleotides. RP2 demonstrated an ability to capture telomerase on an affinity matrix and is useful for purifying telomerase.

The present invention provides novel methods for detecting the RNA component of telomerase. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A method for detecting an RNA component of human telomerase (hTR) in a sample, comprising the steps of:
    (a) contacting the sample with a polynucleotide of at least 7 to about 50 nucleotides in length comprising a sequence that specifically hybridizes to a nucleotide sequence within an accessible region of hTR, wherein the sequence within an accessible region is a sequence selected from nucleotide positions 137–196, 290–319, and 350–380 of hTR but that does not specifically hybridize to a template region of hTR, and
    (b) detecting whether the polynucleotide has specifically hybridized to hTR;
    whereby specific hybridization provides a detection of hTR in the sample.

2. The method of claim 1, wherein the nucleotide sequence of the polynucleotide is substantially complementary to a nucleotide sequence of hTR within and including nucleotide positions 137–196, 290–319, and 350–380.

3. The method of claim 1, wherein the polynucleotide is a nucleotide analog selected from phosphorothioates, phosphoramidates, methyl phosphonates, chiral-methyl phosphonates, 2O-methyl ribonucleotides, and peptide-nucleic acids.

4. The method of claim 1, wherein the polynucleotide is a polynucleotide whose sequence is selected from the group consisting of:

5. The method of claim 1, wherein detection comprises quantitating the amount of hTR in the sample.

6. The method of claim 1, wherein the sample is prepared for in situ detection.

7. The method of claim 1, wherein the sample comprises a histological section of tissue.

8. The method of claim 1, wherein the polynucleotide comprises a detectable moiety, and the step of detecting whether the polynucleotide has specifically hybridized to hTR comprises detecting the moiety.

9. The method of claim 8, wherein the detectable moiety further comprises a linker attached to the polynucleotide.

10. The method of claim 8, wherein the detectable moiety is a fluorescent label, a radioactive label, an enzymatic label, a biotinyl group, and an epitope recognized by a secondary reporter.

11. The method of claim 1, wherein the polynucleotide is a primer and the step of detecting whether the polynucleotide has specifically hybridized to hTR comprises:
    (a) initiating reverse transcription of hTR with the primer, and
    (b) detecting an hTR reverse transcript;
    whereby detection of the reverse transcript indicates that the polynucleotide has specifically hybridized to hTR.

12. The method of claim 11, wherein the reverse transcription comprises chain elongation of sequences complementary to hTR with a nucleotide comprising a detectable moiety, and the step of detecting an hTR reverse transcript comprises detecting the moiety, whereby the detection of the moiety provides a detection of the reverse transcript.

13. The method of claim 12, wherein the detectable moiety is a fluorescent label, a radioactive label, an enzymatic label, a biotinyl group, and an epitope recognized by a secondary reporter.

14. The method of claim 11, wherein the step of detecting an hTR reverse transcript comprises:
(a) contacting the sample with a polynucleotide probe comprising a detectable moiety, and
(b) detecting hybridization between the probe and the reverse transcript by detecting the moiety;
whereby hybridization between the polynucleotide probe and the reverse transcript provides detection of the hTR reverse transcript.

15. The method of claim 14, wherein the detectable moiety is a fluorescent label, a radioactive label, an enzymatic label, a biotinyl group, and an epitope recognized by a secondary reporter.

16. The method of claim 11, wherein the step of detecting the reverse transcript comprises the steps of amplifying a sequence of hTR from the reverse transcript, and detecting an amplified hTR sequence and its complement; whereby detection of an amplified hTR sequence and its complement provides detection of the reverse transcript.

17. The method of claim 16, wherein the step of amplifying a sequence of hTR comprises including a primer incorporating a nucleotide comprising a detectable moiety, and the step of detecting an amplified hTR sequence and its complement comprises detecting the moiety; whereby the detection of the moiety provides detection of the amplified hTR sequence and its complement.

18. The method of claim 17, wherein the detectable moiety is a fluorescent label, a radioactive label, an enzymatic label, a biotinyl group, and an epitope recognized by a secondary reporter.

19. The method of claim 16, wherein the step of detecting an amplified hTR sequence and its complement comprises:
(a) contacting the sample after said amplifying step with a polynucleotide probe comprising a detectable moiety, and
(b) detecting hybridization between the probe and an amplified hTR sequence and its complement by detecting the moiety;
whereby hybridization between the polynucleotide probe and the amplified hTR sequence and its complement provides detection of the amplified hTR sequence and its complement.

20. The method of claim 19, wherein the detectable moiety is a fluorescent label, a radioactive label, an enzymatic label, a biotinyl group, and an epitope recognized by a secondary reporter.

21. A method for diagnosing cancer in a patient, comprising the steps of:
(a) determining a diagnostic value by detecting the RNA component of human telomerase (hTR) in a patient sample, wherein detecting hTR comprises the steps of:
(i) contacting the sample with a polynucleotide of at least 7 to about 50 nucleotides in length comprising a sequence that specifically hybridizes to a nucleotide sequence within an accessible region of hTR, wherein the sequence within an accessible region is a sequence selected from nucleotide positions 137–196, 290–319, and 350–380 of hTR, but that does not specifically hybridize to a template region of hTR, and
(ii) detecting specific hybridization of the polynucleotide to hTR;
whereby specific hybridization provides a determination that the sample contains hTR, and
(b) comparing the diagnostic value with a normal range of hTR in control cells;
whereby a diagnostic value that is above the normal range is diagnostic of cancer.

22. The method of claim 21, wherein the cancer is bladder, colon, breast, and prostate.

23. A method for providing a prognosis for a cancer patient, comprising the steps of:
(a) determining the amount of the RNA component of human telomerase (hTR) per cancer cell in a patient sample comprising cancer cells by:
(i) contacting the sample with a polynucleotide of at least 7 nucleotides to about 50 nucleotides in length comprising a sequence that specifically hybridizes to a nucleotide sequence within an accessible region of hTR, wherein the sequence within an accessible region is a sequence selected from nucleotide positions 137–196, 290–319, and 350–380 of hTR, but that does not specifically hybridize to a template region of hTR,
(ii) determining the amount of polynucleotide that has specifically hybridized to hTR, and
(iii) correlating the amount of polynucleotide with an amount of hTR per cancer cell in the sample; and
(b) comparing the amount of hTR per cancer cell with a prognostic value of hTR per cancer cell consistent with a prognosis for the cancer;
whereby an amount of hTR per cell in the sample that is at the prognostic value provides the particular prognosis.

24. The method of claim 23, wherein the cancer is neuroblastoma, colon, breast, and prostate.

25. A method of determining the amount of the RNA component of human telomerase (hTR) in a sample, comprising the steps of:
(a) amplifying from the sample a sequence from an accessible region of hTR, wherein the region comprises nucleotide positions 137–196, 290–319, and 350–380 of hTR, to produce amplified hTR,
(b) amplifying from the sample a control polynucleotide to produce amplified control polynucleotide,
(c) determining an amount of amplified hTR and an amount of amplified control polynucleotide in the sample, and
(d) normalizing the amount of amplified hTR with respect to the amount of amplified control polynucleotide to provide a normalized amount of hTR,
whereby the normalized amount of hTR provides a determination of the amount of hTR in the sample.

26. The method of claim 25, wherein the control polynucleotide is rRNA.

27. The method of claim 26, wherein the rRNA is 28S rRNA.

28. The method of claim 25, wherein the efficiency of amplification of the control polynucleotide is different than the efficiency of amplification of hTR.

29. The method of claim 25, wherein the efficiency of amplification of the control polynucleotide is less than the efficiency of the amplification of hTR.

30. The method of claim 25, wherein said control polynucleotide is an RNA, further comprising the step, before amplifying, of initiating reverse transcription of hTR from a primer that hybridizes to hTR and initiating reverse transcription of the control polynucleotide from a primer that hybridizes to the control polynucleotide, under conditions such that initiating reverse transcription of the control polynucleotide is less efficient than initiating reverse transcription of hTR.

31. The method of claim 25, wherein the step of amplifying a sequence of hTR comprises:

(a) initiating chain elongation of an hTR complementary sequence from a primer that hybridizes to a polynucleotide having the hTR sequence, and (b) initiating chain elongation of the hTR sequence from a primer that hybridizes to a polynucleotide having the hTR complementary sequence;

and the step of amplifying a sequence from the control polynucleotide comprises:

(a) initiating chain elongation of a control polynucleotide complementary sequence from a primer that hybridizes to a polynucleotide having the control polynucleotide sequence, and (b) initiating chain elongation of the control sequence from a primer that hybridizes to a polynucleotide having the control polynucleotide sequence;

wherein the conditions are selected such that the combined efficiency of initiating chain elongation of the control polynucleotide sequence and complementary sequence is less than the combined efficiency of initiating chain elongation of the hTR sequence and complementary sequence.

32. The method of claim 25, wherein a difference in the combined efficiency of initiating chain elongation of the hTR sequence and complementary sequence, and the combined efficiency of initiating chain elongation of the control polynucleotide and complementary sequence, is about the same as a difference in the amount of hTR and the control polynucleotide.

33. The method of claim 25, wherein the combined efficiency of hybridization of the primers that hybridize to the control polynucleotide sequence and complementary sequence is less than the combined efficiency of hybridization of the primers that hybridize to the hTR sequence and the hTR complementary sequence.

34. The method of claim 25, wherein the combined length of the primers that hybridize to the control polynucleotide sequence and the complementary sequence is shorter than the combined length of the primers that hybridize to the hTR sequence and the hTR complementary sequence.

35. The method of claim 25, wherein at least one primer that hybridizes to the control polynucleotide sequence and the control polynucleotide complementary sequence comprises mismatches with the control polynucleotide sequence and the control polynucleotide complementary sequence.

36. The method of claim 25, wherein the control polynucleotide is amplified with a first primer and a second primer having a sequence selected from the group consisting of:

GCT AAA TAC CGG CAC GAG ACC GAT AG (SEQ ID NO:15)
GCT AAA TAC CGG CAC GAG AC (SEQ ID NO:16)
GCT AAA TAC CGG CAC GAG (SEQ ID NO:17)
GAT CTA AAT ACC GGC ACG (SEQ ID NO:18)
GAG CTA AAT ACC GGC ACG (SEQ ID NO:19)
GGT TTC ACG CCC TCT TGA ACT CTC TC (SEQ ID NO:20)
GTT TCA CGC CCT CTT GAA CTC (SEQ ID NO:21)
GTT TCA CGC CCT CTT GAA C (SEQ ID NO:22)
CTA GTT TCA CGC CCT CTT G (SEQ ID NO:23)
CTG GTT TCA CGC CCT CTT G(SEQ ID NO:24).

37. The method of claim 1, wherein the polynucleotide is DNA.

38. The method of claim 1, wherein the polynucleotide is RNA.

* * * * *

UNITED STATES PATENT AND TRADEMARK OFFICE
CERTIFICATE OF CORRECTION

PATENT NO.    : 5,846,723                                         Page 1 of 1
DATED         : December 8, 1998
INVENTOR(S)   : Kim et al.

It is certified that error appears in the above-identified patent and that said Letters Patent is hereby corrected as shown below:

Column 33,
Line 67, after the phrase "group consisting of:", please insert the following:

CGT TCC TCT TCC TGC GGC CTG AAA CGG TGA (SEQ ID NO:2)
CGT TCC TCT TCC TGC GGC CT (SEQ ID NO:3)
CGT TCC TCT TCC (SEQ ID NO:4)
CTG ACA GAG CCC AAC TCT TCG CGG TGG CAG (SEQ ID NO:5)
CTG ACA GAG CCC AAC TCT TC (SEQ ID NO:6)
CCA ACT CTT CGC GGT GGC AG (SEQ ID NO:7)
GCT CTA GAA TGA ACG GTG GAA GGC GGC AGG (SEQ ID NO:8)
GCT CTA GAA TGA ACG GTG G (SEQ ID NO:9)
GCT CTA GAA TGA ACG (SEQ ID NO:10)
GCT CTA GAA TG (SEQ ID NO:11)
GCT CTA G (SEQ ID NO:12)
CAT TTT TTG TTT GCT CTA GA (SEQ ID NO:13) and
CGG GCC AGC AGC TGA CA (SEQ ID NO:14)

Signed and Sealed this

Twenty-eighth Day of May, 2002

Attest:

JAMES E. ROGAN
Attesting Officer    Director of the United States Patent and Trademark Office

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
( A ) LENGTH: 981 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| CTGCAGAGGA | TAGAAAAAAG | WCCCTCTGAT | ACCTCAAGTT | AGTTTCACCT | TTAAAGAAGG | 60 |
| TCGGAAGTAA | AGACGCAAAG | CCTTTCCCGG | ACGTGCGGAA | GGGCAACGTC | CTTCCTCATG | 120 |
| GCCGGAAATG | GAACTTTAAT | TTCCCGTTCC | CCCCAACCAG | CCCGCCCGAG | AGAGTGACTC | 180 |
| TCACGAGAGC | CGCGAGAGTC | AGCTTGGCCA | ATCCGTGCGG | TCGGCGGCCG | CTCCCTTTAT | 240 |
| AAGCCGACTC | GCCCGGCAGC | GCACCGGGTT | GCGGAGGGTG | GGCCTGGGAG | GGGTGGTGGC | 300 |
| CATTTTTTGT | CTAACCCTAA | CTGAGAAGGG | CGTAGGCGCC | GTGCTTTTGC | TCCCCGCGCG | 360 |
| CTGTTTTTCT | CGCTGACTTT | CAGCGGGCGG | AAAAGCCTCG | GCCTGCCGCC | TTCCACCGTT | 420 |
| CATTCTAGAG | CAAACAAAAA | ATGTCAGCTG | CTGGCCCGTT | CGCCCCTCCC | GGGGACCTGC | 480 |
| GGCGGGTCGC | CTGCCCAGCC | CCCGAACCCC | GCCTGGAGGC | CGCGGTCGGC | CCGGGGCTTC | 540 |
| TCCGGAGGCA | CCCACTGCCA | CCGCGAAGAG | TTGGGCTCTG | TCAGCCGCGG | GTCTCTCGGG | 600 |
| GGCGAGGGCG | AGGTTCAGGC | CTTTCAGGCC | GCAGGAAGAG | GAACGGAGCG | AGTCCCCGCG | 660 |
| CGCGGCGCGA | TTCCCTGAGC | TGTGGGACGT | GCACCAGGA | CTCGGCTCAC | ACATGCAGTT | 720 |
| CGCTTTCCTG | TTGGTGGGGG | GAACGCCGAT | CGTGCGCATC | CGTCACCCCT | CGCCGGCAGT | 780 |
| GGGGGCTTGT | GAACCCCCAA | ACCTGACTGA | CTGGGCCAGT | GTGCTGCAAA | TTGGCAGGAG | 840 |
| ACGTGAAGGC | ACCTCCAAAG | TCGGCCAAAA | TGAATGGGCA | GTGAGCCGGG | GTTGCCTGGA | 900 |
| GCCGTTCCTG | CGTGGGTTCT | CCCGTCTTCC | GCTTTTTGTT | GCCTTTATG | GTTGTATTAC | 960 |
| AACTTAGTTC | CTGCTCTGCA | G | | | | 981 |

( 2 ) INFORMATION FOR SEQ ID NO:2:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:2:

CGTTCCTCTT CCTGCGGCCT GAAACGGTGA 30

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

CGTTCCTCTT CCTGCGGCCT 20

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

CGTTCCTCTT CC 12

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

CTGACAGAGC CCAACTCTTC GCGGTGGCAG 30

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

CTGACAGAGC CCAACTCTTC 20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

CCAACTCTTC GCGGTGGCAG 20

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GCTCTAGAAT GAACGGTGGA AGGCGGCAGG          30

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

GCTCTAGAAT GAACGGTGG          19

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

GCTCTAGAAT GAACG          15

( 2 ) INFORMATION FOR SEQ ID NO:11:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

GCTCTAGAAT G          11

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

CCTGCGGCCT GAAACGGTGA          20

( 2 ) INFORMATION FOR SEQ ID NO:13:

( i ) SEQUENCE CHARACTERISTICS:
        ( A ) LENGTH: 20 base pairs (B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:13:

CATTTTTTGT TTGCTCTAGA 20

(2) INFORMATION FOR SEQ ID NO:14:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:14:

CGGGCCAGCA GCTGACA 17

(2) INFORMATION FOR SEQ ID NO:15:

(i) SEQUENCE CHARACTERISTICS:
(A) LENGTH: 26 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:15:

GCTAAATACC GGCACGAGAC CGATAG 26

(2) INFORMATION FOR SEQ ID NO:16:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:16:

GCTAAATACC GGCACGAGAC 20

(2) INFORMATION FOR SEQ ID NO:17:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:17:

GCTAAATACC GGCACGAG 18

(2) INFORMATION FOR SEQ ID NO:18:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA ( x i ) SEQUENCE DESCRIPTION: SEQ ID NO:18:

GATCTAAATA CCGGCACG 18

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

GAGCTAAATA CCGGCACG 18

( 2 ) INFORMATION FOR SEQ ID NO:20:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

GGTTTCACGC CCTCTTGAAC TCTCTC 26

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

GTTTCACGCC CTCTTGAACT C 21

( 2 ) INFORMATION FOR SEQ ID NO:22:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

GTTTCACGCC CTCTTGAAC 19

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

CTAGTTTCAC GCCCTCTTG 19

(2) INFORMATION FOR SEQ ID NO:24:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:24:

CTGGTTTCAC GCCCTCTTG                    19

(2) INFORMATION FOR SEQ ID NO:25:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:25:

GAAGGGCGTA GGCGCCGTGC TTTTGC            26

(2) INFORMATION FOR SEQ ID NO:26:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:26:

GTTTGCTCTA GAATGAACGG TGGAAGG           27